(12) United States Patent
Borich et al.

(10) Patent No.: US 7,267,799 B1
(45) Date of Patent: *Sep. 11, 2007

(54) UNIVERSAL OPTICAL IMAGING AND PROCESSING SYSTEM

(75) Inventors: Damon Vincent Borich, Austin, TX (US); William Patrick Coffey, Mission Viejo, CA (US)

(73) Assignee: Detekt Biomedical, L.L.C., Austin, TX (US)

( * ) Notice: Subject to any disclaimer, the term of this patent is extended or adjusted under 35 U.S.C. 154(b) by 579 days.

This patent is subject to a terminal disclaimer.

(21) Appl. No.: 10/640,134

(22) Filed: Aug. 13, 2003

Related U.S. Application Data (60) Provisional application No. 60/403,238, filed on Aug. 14, 2002.

(51) Int. Cl.
*G01N 33/00* (2006.01)
(52) U.S. Cl. .................. 422/82.05; 436/164; 436/43; 436/901; 422/62; 235/462.11; 702/84
(58) Field of Classification Search .................. 422/62, 422/82.05; 436/43, 901; 235/462.11; 702/84
See application file for complete search history.

(56) References Cited

U.S. PATENT DOCUMENTS

| | | | |
|---|---|---|---|
| 5,408,535 A * | 4/1995 | Howard et al. ............. 382/128 |
| 5,580,794 A | 12/1996 | Allen | |
| 5,594,808 A | 1/1997 | Shen et al. | |
| 6,432,720 B2 | 8/2002 | Chow | |
| 6,544,475 B1 | 4/2003 | Douglas et al. | |
| 6,563,653 B2 | 5/2003 | Ramm et al. | |
| 6,565,808 B2 | 5/2003 | Hudak et al. | |
| 6,567,163 B1 | 5/2003 | Sandstrom | |
| 6,576,476 B1 | 6/2003 | Taylor et al. | |
| 6,586,257 B1 | 7/2003 | Vuong | |
| 6,597,450 B1 | 7/2003 | Andrews et al. | |
| 2002/0060247 A1 | 5/2002 | Krishnaswamy et al. | |
| 2003/0027244 A1 | 2/2003 | Colston et al. | |
| 2003/0073931 A1 | 4/2003 | Boecker et al. | |
| 2003/0112432 A1 | 6/2003 | Yguerabide et al. | |
| 2003/0119202 A1 | 6/2003 | Kaylor et al. | |
| 2003/0124738 A1 | 7/2003 | Crosby | |
| 2004/0156555 A1 * | 8/2004 | Irving et al. ............. 382/274 |

* cited by examiner

*Primary Examiner*—Lyle A. Alexander
(74) *Attorney, Agent, or Firm*—Toler Schaffer LLP (57) ABSTRACT

The present disclosure is directed, in general, to an optical reading system, a universal testing cartridge, and a method of coupling optical reading systems. In a particular illustrative embodiment, the optical reading system includes a universal test cartridge receptor, test format determination logic, test criteria determination logic, and an optical reader module. The universal test cartridge receptor is responsive to a universal test cartridge having a test strip inserted therein. The test format determination logic determines an optical test format of the test strip. The test criteria determination logic determines an optical test criteria based upon the optical test format. The optical reader module is configured to capture an optical test image of the test strip.

15 Claims, 9 Drawing Sheets

UNIVERSAL OPTICAL IMAGING AND PROCESSING SYSTEM

CROSS-REFERENCE TO RELATED APPLICATION(S)

The present application claims priority from U.S. provisional patent application No. 60/403,238, filed Aug. 14, 2002, entitled "Universal chemical and biochemical optical imaging and processing system," naming inventors Damon Vincent Borich and William Patrick Coffey, which application is incorporated by reference herein in its entirety.

FIELD OF THE DISCLOSURE

The disclosure relates generally to the field of automated optical detection of analytes in a variety of disposable diagnostic test devices.

BACKGROUND

Numerous systems and instruments have been created to aid in the detection of analytes from a wide variety of mediums. These systems have been created for use in the fields of medical diagnostics, air and water quality monitoring, food and beverage testing, and biothreat detection among several others. These systems range from handheld portable devices such as blood glucometers and portable biothreat detectors to laboratory based instruments, such as spectrometers and automated clinical chemistry detectors. Despite this evolution in automated testing, the majority of these systems interface with a discrete or limited range of samples or sample cartridges and have limited cross-field diagnostic capabilities. These limitations often result from building systems using application specific diagnostic devices that lack hardware, software and processing flexibility to address new test architectures and protocols. As a result, the average consumer or industry technician is faced with a multitude of disparate limited devices with differing operation protocols.

Rapid diagnostic test strips and cartridges have been created to detect a broad range of chemical and biological agents. The majority of these tests attempt to quantify the presence of particular analytes by producing a color change or visible line or zone signifying the analytes presence or level. In the case of multiple analytes, several potential lines or zones of color change are noted. These test devices are available for many analytes ranging from drug metabolites, pregnancy hormones, anthrax, E. Coli, blood glucose, pool ph and chlorine etc. As such, the physical embodiment of these tests varies according to the application and the manufacturer. In some cases the tests may be the size and shape of a stick of gum, a business card, or a thin bookmarker. They generally have a region that is visible by the user for subjective interpretation of the test results.

These test strips are used or activated in a variety of ways. Dependent upon what test and protocol the user is employing, they may dip the strip into a fluid, apply fluid using a dropper, place the strip on a fluid (e.g., blood drop on finger), or expose the strip to ambient conditions. Once the test is activated and the sample is added a set time is generally allowed to elapse. After this set time, the user generally visually inspects the test strip for color changes in the designated regions. These color changes are compared to a reference that indicates threshold levels for quantified analyte levels.

These tests have been in use for several years and continue to be available for an increasing number of analytes due to their ease of use. Recently, due to advances in chemistry and biochemical assay formulation, these tests have been formulated to detect multiple classes of analytes on the same device. As such, the computational algorithms used to interpret tests by these devices are increasing in complexity and would benefit from the use of an adaptable automated device to reliably quantify the test output and store optical test results.

Accordingly, there is a need for a universal optical imaging and processing system.

SUMMARY

The present disclosure is directed, in general, to an optical reading system, a universal testing cartridge, and a method of coupling optical reading systems with a test cartridge.

In a particular illustrative embodiment, the optical reading system includes a universal test cartridge receptor, test format determination logic, test criteria determination logic, and an optical reader module. The universal test cartridge receptor is responsive to a universal test cartridge having a test strip inserted therein. The test format determination logic determines an optical test format of the test strip. The test criteria determination logic determines an optical test criteria based upon the optical test format. The optical reader module is configured to capture an optical test image of the test strip.

In accordance with another exemplary embodiment, a universal testing cartridge that includes a housing is disclosed. The housing receives a selected test strip and is insertable into an optical reading apparatus. The selected test strip has an associated optical testing format. The associated optical testing format of the selected test strip is different than an optical testing format associated with other test strips suitable for insertion into the housing. The optical testing format of the selected test strip has corresponding testing criteria for use by the optical reading apparatus in connection with reading the test strip.

In accordance with another exemplary embodiment, an optical reading system includes a universal test cartridge receptor, test format determination logic, test criteria determination logic, and an optical reader module. The universal test cartridge receptor is responsive to a first type of test cartridge. The first type of test cartridge has a first test strip inserted therein. The universal test cartridge is responsive to a second type of test cartridge having a second test strip inserted therein. The test format determination logic determines an optical test format of the first test strip or the second test strip. The test criteria determination logic determines an optical test criteria based upon the optical test format. The optical reader module is configured to capture an optical test image of either the first test strip or the second test strip. The optical reader module is separable from a computer device including a display device.

In accordance with another exemplary embodiment, a method of coupling an optical reading system having a captured image of a test strip within a test cartridge to a separable computer device having a display is disclosed. The method includes coupling an interface of the optical reading system to an input port of the computer device, communicating data from the interface of the optical reading system to the computer port of the computer device, and displaying an image on the display device. The displayed image is derived from the data received by the input port of the computer device from the interface of the optical reading system. The optical reading system includes a universal test cartridge receptor responsive to a first type of test cartridge having a first test strip inserted therein and responsive to a second type of test cartridge having a second test strip inserted therein.

BRIEF DESCRIPTION OF THE DRAWINGS

The use of the same reference symbols in different drawings indicates similar or identical items.

DESCRIPTION OF THE DRAWINGS

In a particular embodiment, the disclosure is directed to a universal diagnostic platform for optical interrogation of lateral flow, dry chemistry strips and micro-fluidic biochips for chemical and bio-chemical assays utilizing an adaptable imaging device with pattern recognition software algorithms for quantitative data reporting in a customizable software suite. The disclosure describes a universal diagnostic platform for optical interrogation of standard chemical and biochemical assays (e.g. glucose, cholesterol, ph, chlorine, infectious diseases) using sample mediums such as water, blood, urine and saliva. The platform includes four components: a optical reader with digital components; a disposable cartridge with active chemistry; software for interfacing with the user, and an image processing and computing device to interface with the optical reader.

In the particular embodiment, the system accepts a broad range of standard commercially available and custom lateral flow, dry chemistry test strips, and biochips through a standard mechanical interface via an adaptable cartridge housing. The reader performs optical interrogation by imaging the active region of the cartridge chemistry via a complimentary metal-oxide semiconductor (CMOS) or charge-coupled device (CCD) detector. Illumination may be provided by a series of optically tuned light emitting diodes. Raw image data is collected, digitized, and stored in an on-board memory. This information is then processed using a host device (e.g. PDA, laptop, cellular phone) processing capabilities in conjunction with the software component of the system. Software pre-loaded onto the reader provides the processing instructions and compares image analysis data to pre-defined calibration data, yielding a quantitative result. The reader may interface with the host device through several different physical standards. These standards include industry standards such as Personal Computer Memory Card International Association (PCMCIA), Universal Serial Bus (USB), Serial, Secure Digital, BlueTooth®, WiFi or other company specific standards such as the Handspring Springboard Platform™.

In another embodiment, universal software is automated for adaptable chemical and biochemical optical imaging for cross-field testing compatibility. This universal system is intended to be compatible with a wide array of standard commercial lateral flow strips, biochips, and/or disposable chemical and biochemical assays. The system digitizes and objectively quantifies results from tests (such as test strips that are conventionally read by a human manually); stores original images and data into memory for review; and enhances test processing by executing image processing algorithms.

Figure 1:
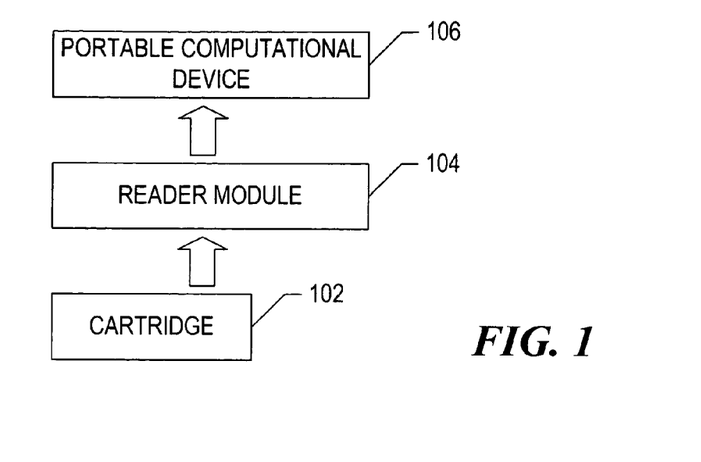
FIGS. 1 and 2 illustrate an exemplary embodiment of an optical reader system.

The exemplary embodiment provides a fully self-contained, universally adaptable handheld automated optical analyzer system and method for acquiring, viewing, interpreting, and reporting results gathered from rapid diagnostic tests and biochips. FIG. 1 demonstrates portable computational circuitry 106, such as a standard PDA or multipurpose handheld circuitry, interfacing with an optical reader 104, which in turn accepts cartridges 102. The reader 104 interfaces with the PDA, for example, through a mechanical interface that provides support structurally and houses the electrical communication ports for the reader 104 and PDA 106. The exemplary embodiment allows the user to hold the instrument in one hand, insert the cartridge into the side of the reader using their other hand and activate the automated software routine.

The reader 104 may alternatively interface with electronics devices other than a PDA including laptop and desktop computers, cellular phones, or other devices that have data input and display components. The interface with these other devices may be through standard ports such as PCMCIA, USB, Firewire, infrared, Wifi, Bluetooth, or other custom communication protocols. The on-board reader includes electronics such as a Field Programmable Gate Array (FPGA) and/or microcontroller that may be re-configured to utilize the appropriate communication protocol. Multiple protocols may be embedded in the reader 104 and may be accessible through standard pre-installed electrical connectors.

Figure 2:
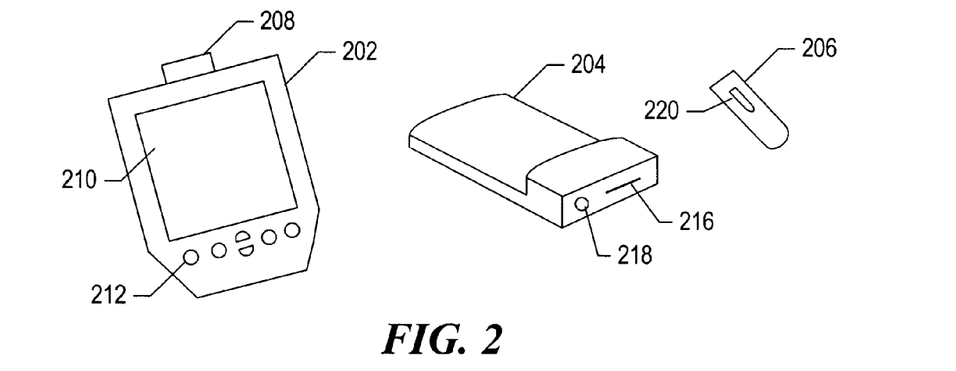

FIG. 2 depicts another exemplary embodiment of an optical reader system. A cartridge 206 may be inserted into an optical reader 204. The optical reader 204 may be attached to a multipurpose handheld device 202, such as a PDA (e.g. those made by VISOR® or Palm). The multipurpose handheld device 202 may include a port or communication interface 208, a display 210, and a button interface 212. The communication interface 208 may be selectively coupled to the reader 204, such as an optical reader, to facilitate the transfer of electro-optical data. Test parameters, test software, and testing data may be manipulated using the button interface 212 or a touch interface integrated with the display 210.

The reader 204 includes a receptor or slot 216 for receiving the cartridge 206. The slot 216 may be located as shown or on a side of the housing containing the reader 204. The reader 204 may also include indicator lights 218. Indicator lights 218 may be used to indicate proper or improper insertion of a cartridge, proper or improper coupling with the circuitry 202, or other states associated with the reader functionality.

The cartridge 206 may be a universal cartridge having one or more windows 220. In one exemplary embodiment, the cartridge 206 may accept test strips of various types. Alternately, test cartridges of various types, sizes, shapes, and chemistries may be provided for reading by the optical reading system.

Figure 3:
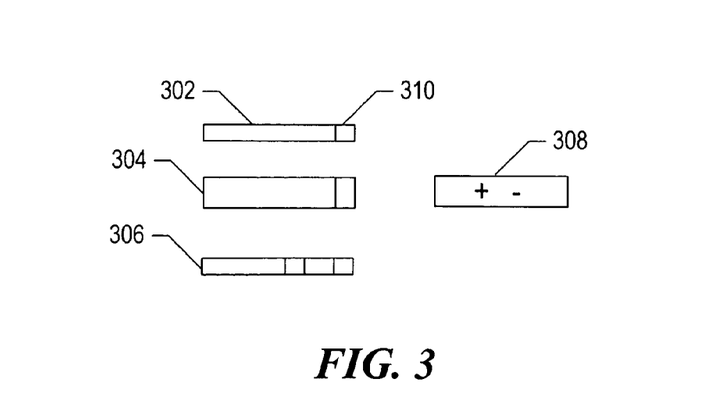
FIG. 3 depicts exemplary embodiments of test strips.

FIG. 3 depicts various types of test strips. Test strips may, for example, be dip test strips, such as strips 302 and 304, lateral flow strips such as strips 306 and 308, or various cards and assay indicators. The strips may have different sizes as indicated by strips 302 and 304. In some exemplary embodiments, the active area of the strip 310 may change color. In some cases, the color to which it changes may indicate concentration. In other exemplary cases, the location of the color change may be important. In still a further example, a shape or lack of a shape may indicate the result of a test. For example, a ketone urine test may change to varying shades indicating varying concentrations. In other examples, a urine pregnancy test may indicate results with a plus sign or negative sign.

Figure 4:
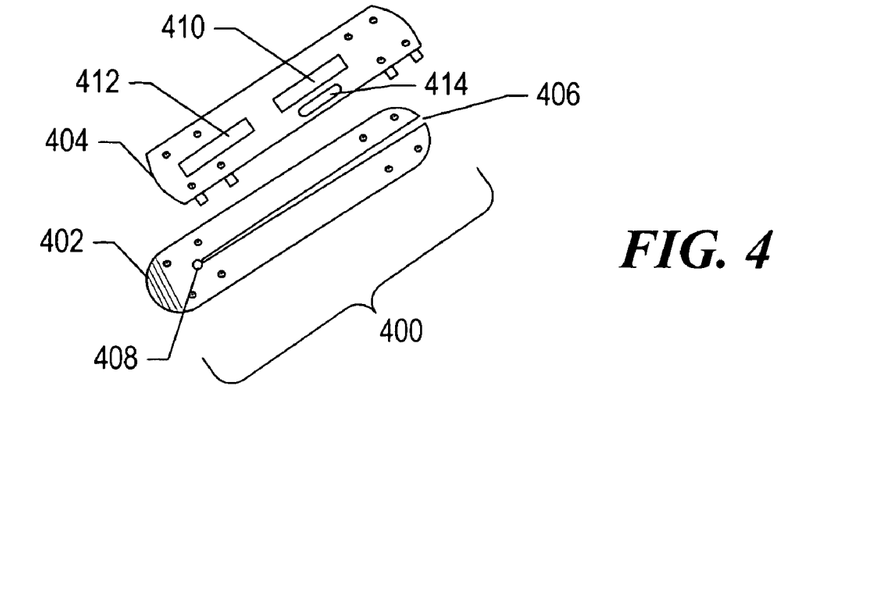
FIG. 4 illustrates an exemplary embodiment of a universal test strip cartridge.

FIG. 4 demonstrates a universal adapter design of an exemplary cartridge. The cartridge may be used to hold a several types of test strips without the use of a separate adapter. This component may be injection molded and may be capable of having a variety of test strips inserted into the clamshell design. The universal adapter positions the strips in such a fashion as to position the test and control lines or zones of interest in view of the proper imaging window 410. Alternately, multiple windows may be provided such as windows 410 and 412.

A top portion 404 of the adapter may overlay a bottom portion 402, enclosing the test strip. The bottom portion 402 may include a central channel 406 for guiding reagent fluid stored in a reagent capsule 408.

Additionally, each adapter has a signature label region 414 that may include a discrete consistent region for coding. This region may be a variety of sizes dependent upon the amount of data storage needed but will generally occupy a 1×1 mm to 1×1 cm space. The coding may include a series of raised, flat, or depressed color dots in a variety of colors. These dots may take an irregular or a regular shape and serve to uniquely identify the cartridge. In other exemplary embodiments, the coding may be an image, lettering, or other identifying marking. Each signature label may be unique and upon manufacture may be imaged and referenced to the appropriate database. These unique signatures may be captured during the imaging process and may then be compared to the pre-established database for identification purposes.

Data stored in these signature labels or in the associated database may include pre-determined test lot data, calibration coefficients, optical standards, expiration dates, illumination requirements, etc. Additionally, this signature label region may include temperature or chemical sensitive dyes that alter their color dependent upon exposure history and may serve as an automated quality control measure.

Figure 5A:
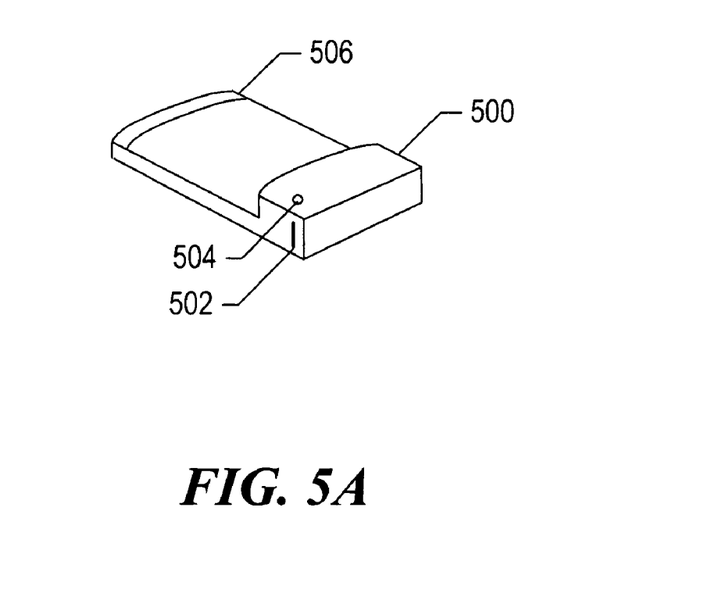
FIGS. 5A, 5B, and 5C depict an exemplary embodiment of an optical reader.
Figure 5B:
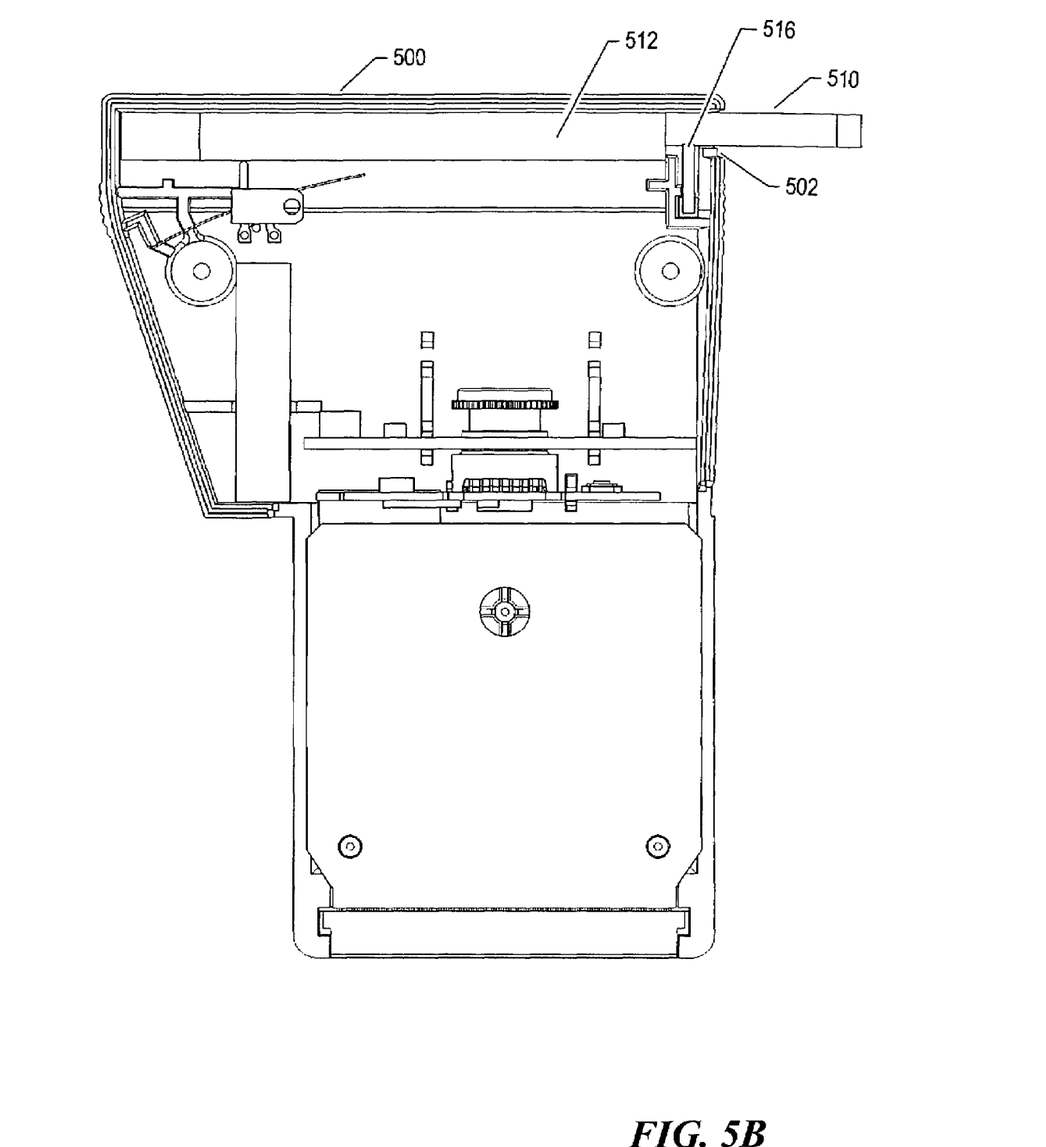
Figure 5C:
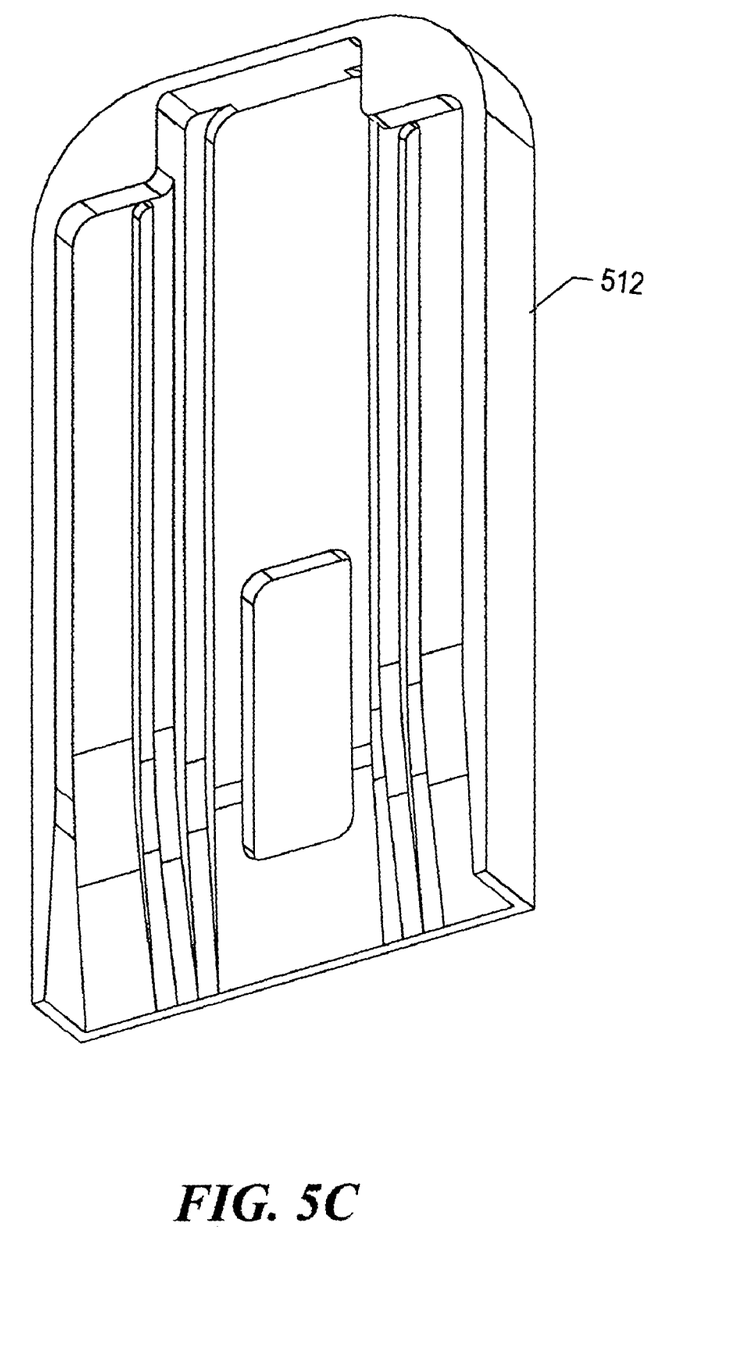

FIGS. 5A, 5B, and 5C depict an exemplary embodiment of the optical reader. The optical reader includes a housing 500 having a slot 502 for inserting a cartridge. The reader also includes an indicator light 504 and a communications interface or port 506. The reader may be coupled to a host device or may be separable from the host device.

FIG. 5B shows an internal view of the optical reader. A cartridge 510 may be inserted into the reader through slot 502. A guide piece 512 may accept the cartridge and guide it into position. For example, the guide piece may guide the cartridge to a centered position. The imaging system 514 may capture an image of the cartridge and transfer that image to analysis systems. In this particular example, the imaging system 514 is positioned such that it has a direct view of the cartridge without using mirrors that may distort the image and require further image processing. The image system may include a CCD, CMOS, or other imaging circuitry.

The reader may also have a gate 516 to block light from outside the reader. Internal light sources such as LEDs may be provided in various wavelengths to illuminate a test strip and provide enhanced frequency profiles for observing various test strips.

FIG. 5C depicts an exemplary guide or receptor 512. In addition to the adaptability of the universal cartridge adapter to different test strip formats, the reader's internal track design, which accepts and guides the cartridge adapters, is itself capable of accepting a variety of cartridge adapters. The internal track design may be a removable injection molded or machined piece that may be replaced dependent upon the users preferences. The internal track design in conjunction with the cartridge adapter serve to accurately position each cartridge and hence test strip according to pre-defined positioning criteria. The track design provides three-axis positioning accuracy of each inserted adapter using a floating tensioning mechanism.

The exemplary guide has various channels with different depths and widths. The guide positions various shaped cartridges to a centered position for imaging.

In one exemplary embodiment, the insertion method allows the user to view the strip during insertion and ensures proper orientation. This method also helps reduce the potential for ambient light leakage into the interior of the housing from external overhead light sources. The side insertion method also allows for longer cartridges to be accommodated as the back wall may be removed to allow the cartridge to pass completely through the reader. Insertion of the cartridge by the user is aided by an internal track design that guides the universal adapter along a predefined course. Insertion of the cartridge fully into the appropriate track activates the reader via a microswitch. This initiates the software routine, which then images the cartridge, retrieves the signature label data, references the stored databases, and completes the optical imaging and processing of the sample.

Figure 6:
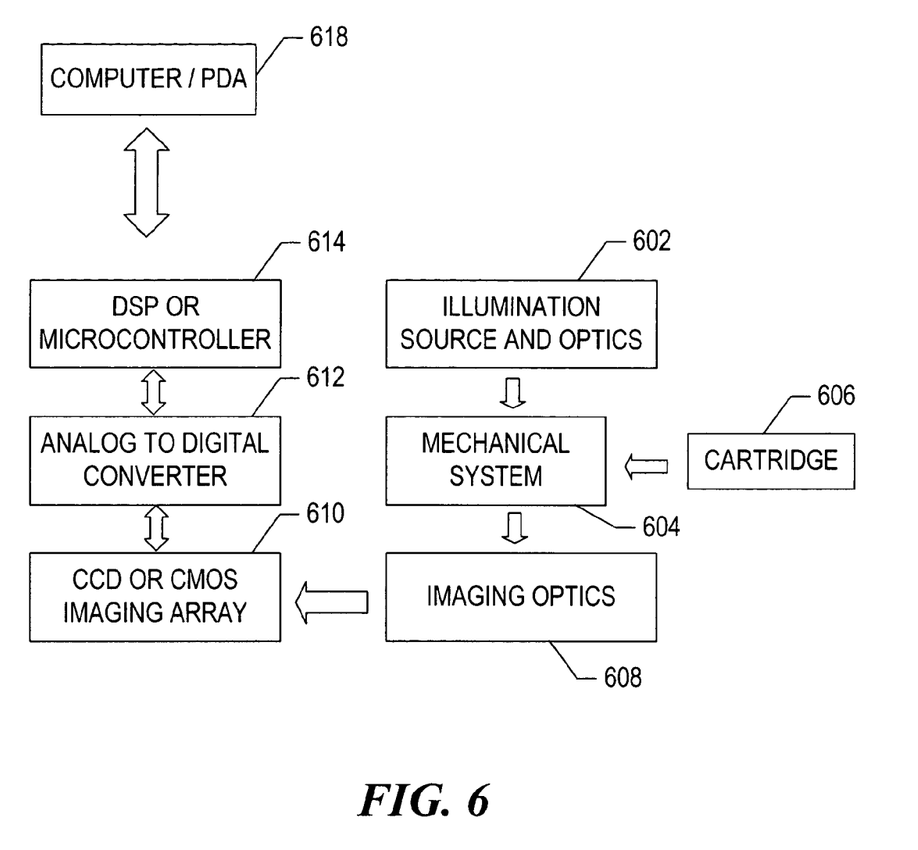
FIG. 6 shows a block diagram of an exemplary circuitry.

FIG. 6 illustrates a general block diagram design of an embodiment of the optical reader. The optical reader has electronics that include a standard CMOS or CCD imaging module 610, digital signal processor (DSP) 614, illumination driver board 602, mechanical system 604, imaging optics 608, and analog to digital converter 612. The reader may also include a microcontroller, FPGA, battery with recharge circuit, indicator lights, and flash memory (not shown). The reader may be designed in such a fashion to be used in a stand-alone application or interfaced with a host computing device 618 via the reconfigurable electrical communication interface. The core electronics are capable of being controlled by the on board micro-controller and FPGA and may be programmed to interface with multiple devices. A standard bus design allows the addition of future add-on components without altering the existing hardware. These add-ons may include a Global Position System (GPS) module that records the testing location of the reader, a Radio Frequency Identification (RFID) reader that scans the inserted cartridges for data and writes the results to the cartridge for post-testing verification, and additional sensors and probes for detection of other analytes such as airborne contaminants.

In general, the illumination source 602 may direct light or electromagnetic energy on a cartridge 606 inserted into the mechanical system 604. The illumination source 602 may vary the intensity or wavelength of light in accordance with the testing criteria associated with the cartridge. In other embodiments, a white light source or set of sources covering multiple wavelengths may be used for each cartridge.

Light reflecting from the cartridge 606 may be collected by imaging optics 608 and converted to a signal by the CMOS or CCD imaging array 610. A converter 612 may convert the signal to a digital output for use by the DSP or microcontroller 614. The data may be processed by the reader or transferred to a computer or PDA 618 for further analysis.

Figure 7A:
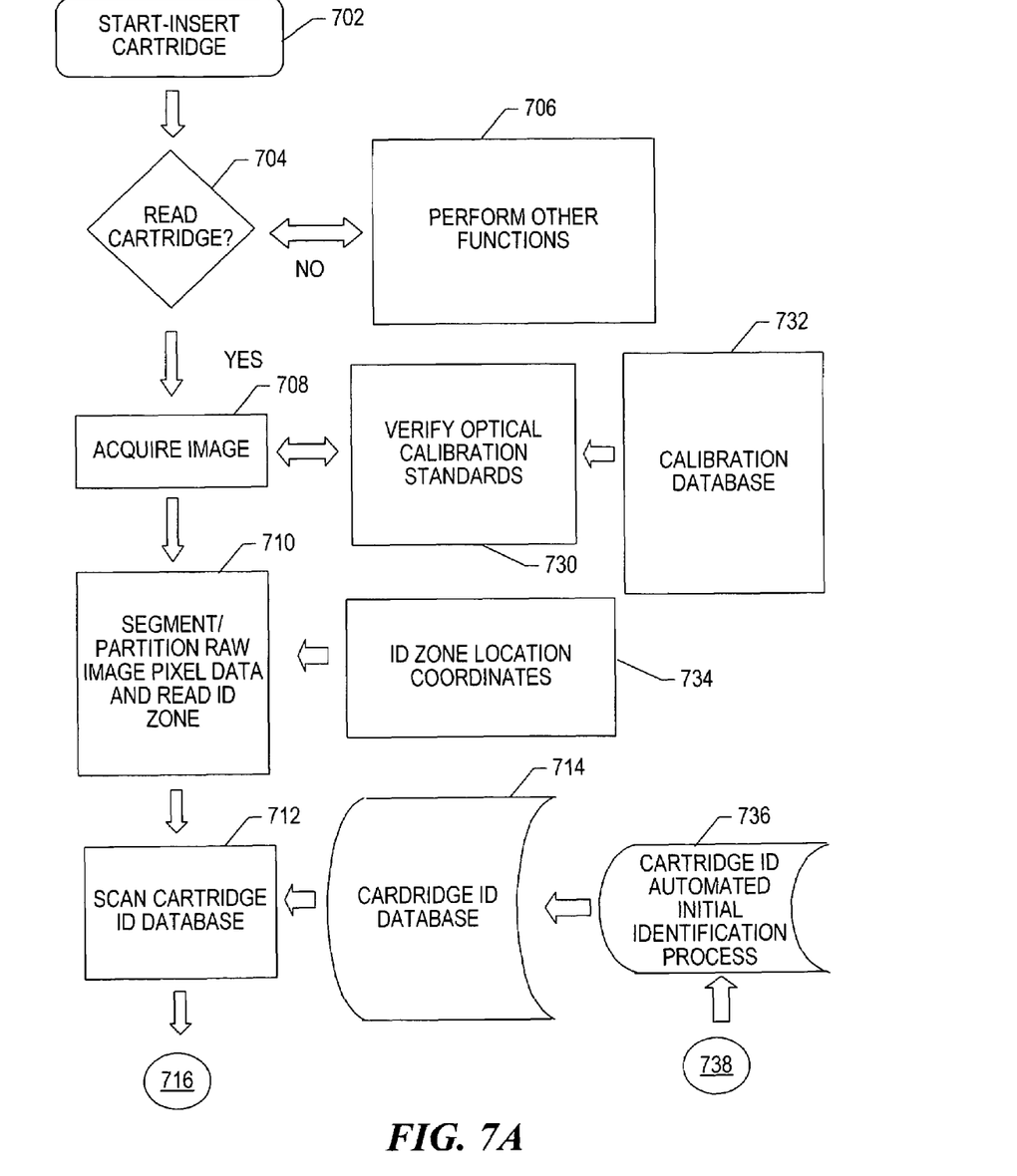
FIGS. 7A and 7B depicts an exemplary method of the system level testing architecture sequence.
Figure 7B:
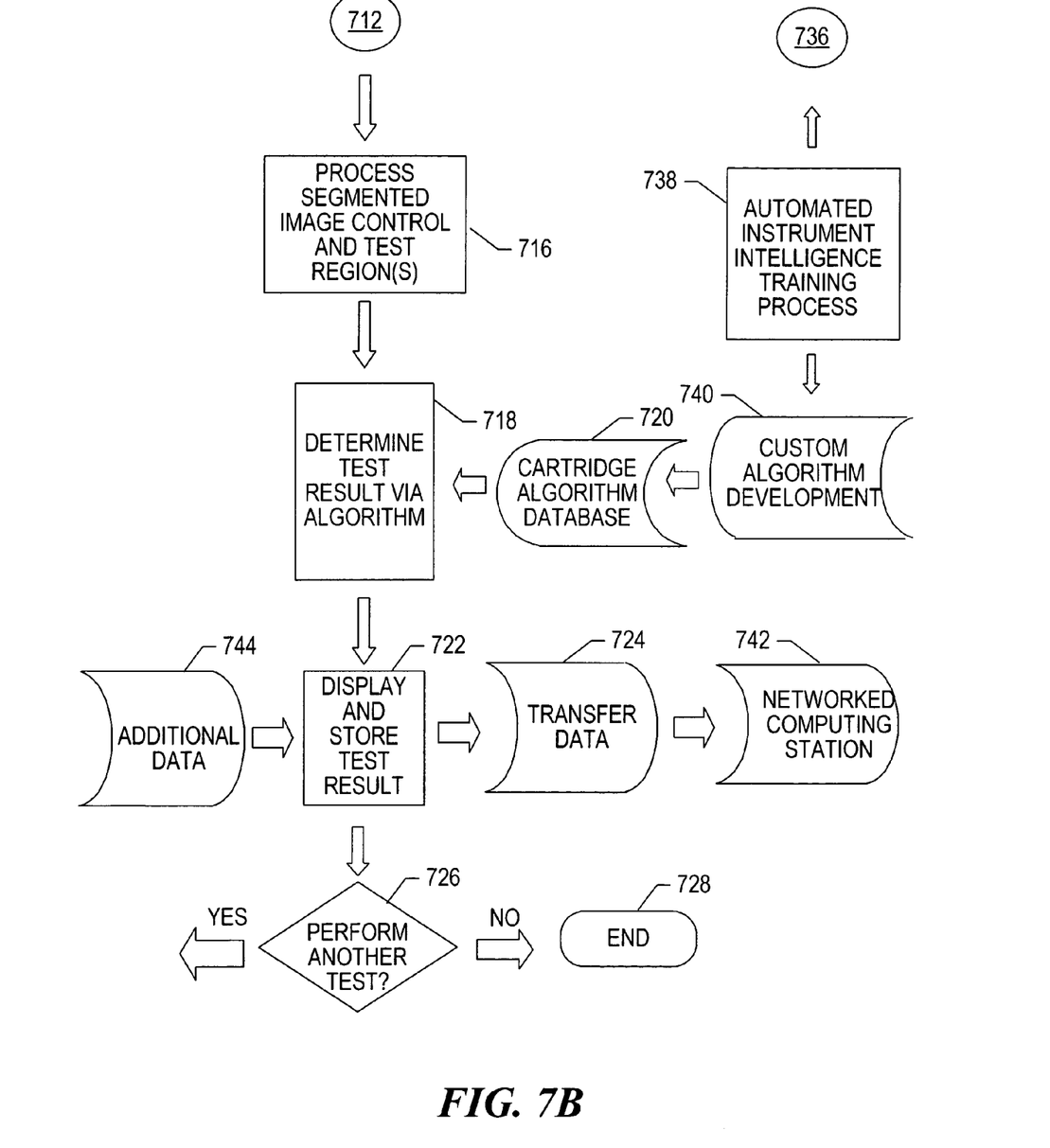

An exemplary method to read and analyze a test cartridge is shown in FIGS. 7A and 7B. The method begins as shown at step 702. The process may start through initiation by a user, attachment of the reader to a PDA or computational device, insertion of a cartridge, upon the expiration of a time period, or some other event. A determination is made as to whether to read a cartridge, as shown at step 704. The user may be prompted or a switch indicating the presence of a cartridge may be checked. If the cartridge is not to be read, other options may be provided to the user as shown at step 706, such as performing a utility, ordering supplies, reviewing training or demonstrations, performing inventory, reviewing past results, or networking.

If the cartridge is to be read, the reader may acquire an image as shown at step 708. In conjunction with the acquisition of the image, the reader may verify calibrations as shown at step 730. This verification may involve reviewing the image in the region of calibration areas on the instrument or cartridge. The calibration may further use a calibration database 732 to store and retrieve calibration data, such as known standards results or optical qualities.

The image may be segmented and an identity zone may be isolated or read as shown at step 710. The identity zone may be a pre-defined location or set of coordinates 734. This identity zone may contain a bar code, a set of colored shapes, images, or lettering. Utilizing the image data from the identity zone, the identity of the cartridge may be determined, as shown at step 712. For example, colors in the identity zone may be matched with patterns stored in a database 714. The database 714 may store information about the cartridge, such as cartridge type, lot, expiration date, and imaging protocol. In addition, the identity database 714 may be adapted through an initial identification process as shown in step 736. For new cartridges or to adapt existing data, an automated instrument intelligence training process, as shown in step 738, may be performed. This process may act to adapt the database 714.

Using the identification data, the system may process the image as shown at step 716. A test determination logic may be used to determine an optical test format. The format may, for example, direct the processing of specific zones in the image, such as a control region and a sample testing region. The processing may result in a test result as shown in step 718. A test criteria determination logic may be used to determine an optical test criteria. This test criteria may be determined through reference to a cartridge algorithm database 720. The cartridge database 720 may, for example, hold calibration sequences, processing algorithms, color mappings, patterns for pattern recognition, or other suitable test criteria for the received cartridge. For example, a shape-based test may be retrieved from database or memory that includes a plurality of available shape-based tests. Evaluation logic may apply the test criteria to data acquired from the image. The processing and determining steps may be performed on the reader or in coupled computation circuitry such as within a host PDA. Users may also adapt the cartridge algorithm database 720 using the automated instrument intelligence training process 738 and a custom algorithm development step 740.

The test results are then displayed as shown at step 722. Additional data 744 may be associated with the results such as Global Positioning System (GPS) data, pH, temperatures, humidity, and other environmental conditions. The reader may include additional instruments with sensors appropriate for gathering the additional data or the data may be acquired from other sources. These results may be displayed on a PDA or by other computing circuitry. The display image may be derived from the data received by the input port. The results may be further uploaded to a server, personal computer, or other computational circuitry 742 for long term storage and access, as shown at step 724. Access may be provided through a website or other network connection.

In one embodiment, the data is stored on the handheld until it is transferred to either the host device or is uploaded to a secure site. This upload process may include communication via wireless technologies such as WiFi, 802.11, or other similar standards.

Data may be transferred in its raw format for secondary analysis along with the pre-processed data. The data may include, in addition to the test results and image, information identifying the user, time of test, location, error status, and/or environmental conditions at time of test.

The system may prompt the user for performing another test, as shown at step 726. If another test is to be performed, the system may return to step 702. If another test is not performed, the method may end as shown at step 728.

Software may serve to automate both the user interface experience and the process of data acquisition and reporting. The software may be built upon a premise that the user simply inserts the cartridge into the reader and the remainder of the tasks are either automated or prompted via the user interface. The process may be performed on the reader, on the portable or multipurpose circuitry, or on a combination of the reader and the circuitry.

Image processing algorithms may be used to interpret the image data against predetermined criteria. The image processing algorithms that can be used are numerous and vary depending upon the type of test being run, the sample conditions, the desired result sensitivity and other variable affects such as background contamination, signal to noise conditions, and overall quality of the test sample. Examples of the basic algorithms include the following:

1) Signal Averaging over entire Area—Average pixel intensities for each optical channel (e.g. Red, Green, Blue) are recorded for the entire selected areas. These are reported as a ratio to one another (i.e. R/G or R/B or R+G/B etc.) or simply as R,G,B values.

2) High/Low difference averaging—The lowest pixel value is subtracted from the highest pixel value for each pixel row and/or column and the difference is reported and averaged across either all the rows or all the columns or any combination therein.

3) Variance Measurement of Averages—The statistical variance in the pixel intensity for each row or column of pixel data is calculated and the variances are averaged either across rows, columns, or combinations therein. Additional weight or scaling factors may be given to a particular channel (RGB) versus another.

Figure 8A:
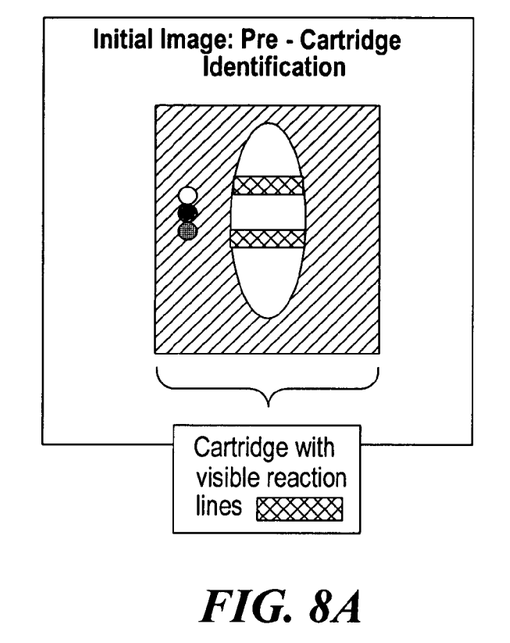
FIGS. 8A and 8B depict exemplary test images.
Figure 8B:
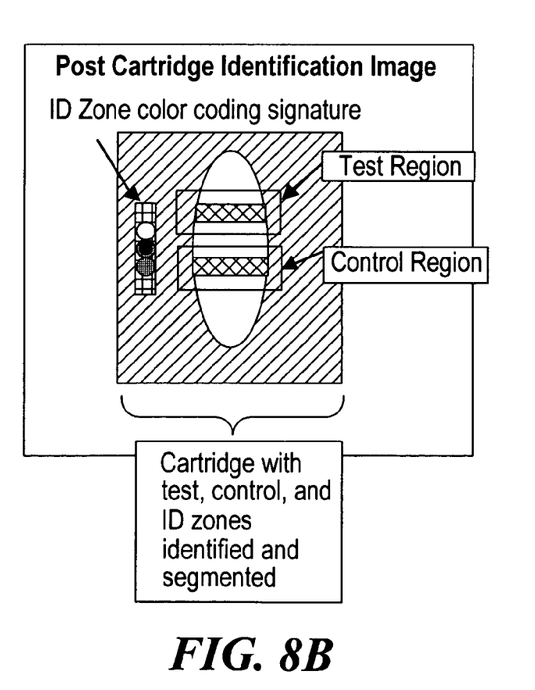

FIGS. 8A and 8B illustrate an exemplary raw cartridge data acquisition and the processing and graphical representation of the data. The data collected and analyzed by the reader may be stored and disseminated in several fashions.

The image shown in FIG. 8A is acquired by the CMOS or CCD detector. As shown in FIG. 8B, the identity zone is isolated and read. This reading may provide data regarding the location of test and control regions, either directly or through reference to a database. The test and control regions can then be isolated and analyzed. These regions may also be stored or displayed as separate files or images.

Figure 9:
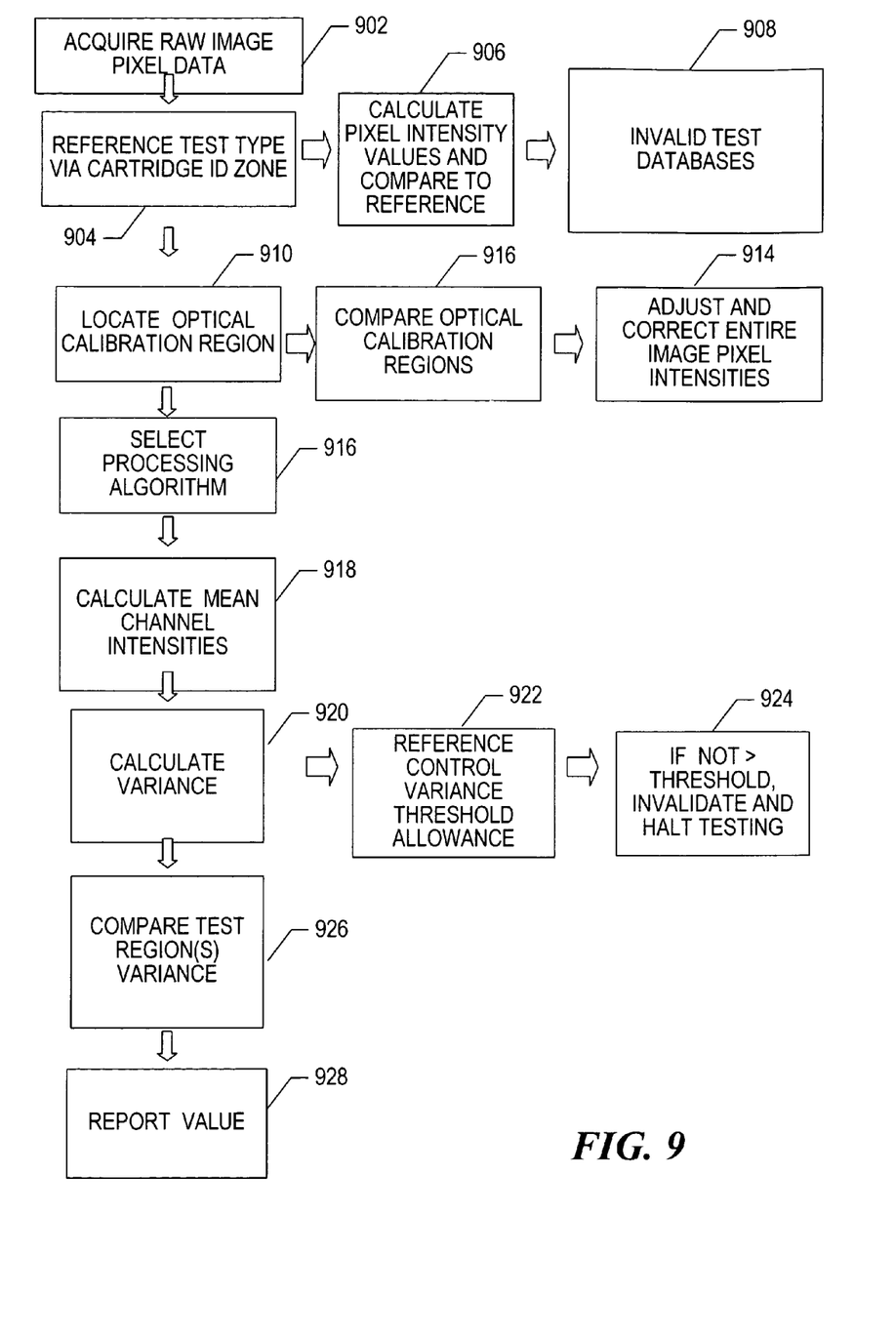
FIG. 9 depicts an exemplary method of an algorithm based optical test analysis.

FIG. 9 depicts an exemplary image processing method. An image is acquired, as shown at step 902. The image detector may be a CMOS, CCD or other detector. The cartridge type is determined via the identity zone of the image, as shown at step 904. A test may also be performed on the cartridge to determine if the cartridge or test is valid. For example, as shown at step 906, mean segment region pixel intensity may be determined and compared to references within an invalid test database 908. The invalid test database 908 may store high and low mean pixel thresholds, cutoffs, and ratios for individual tests.

Once the cartridge is identified, an optical calibration region may be determined, as shown at step 910. Pixel intensity values may be determined for the optical calibration regions and compared to a calibration database, as shown in step 912. Adjustments may be made to correct the image, such as adjusting ratios and intensities of the image so that the calibration regions match pre-set reference levels.

Based on the cartridge identity, a processing algorithm may be selected from a test database, as shown at step 916. In one exemplary algorithm, the pixel row and column mean channel intensities may be calculated for individual regions, as shown at step 918. As shown at step 920, the variance in row and column pixel intensities may be calculated for individual regions. These variances may be compared to threshold allowance values, as shown in step 922. If the control variance is not greater than a threshold, the test may be invalidated and halted.

The test region variance may be compared to a set of test result threshold values, as shown at step 926. These thresholds may be predetermined thresholds for a particular cartridge type. After performing the comparison to the threshold level a result is determined. The test results and other information may then be reported to a user, as shown at step 928.

In one particular example, the exemplary system includes three components: the universal cartridge adapter, the optical reader and electronics, and the processing software. These components are all packaged into a handheld system that can be mated with a variety of host devices such as a PDA, cell phone, laptop or desktop computer.

The universal cartridge adapter may be constructed from injection-molded plastic and serves as a universal housing for standard lateral flow, micro-fluidic biochip, and dry chemistry test strips. The cartridge adapter has a sample application area, a visible area for control and test detection, and an area for sample overflow. The cartridge also has an optical coding region that may consists of a series of discrete colors and shapes to provide a unique signature label to the cartridge. This signature label may be imaged by the optical detector and interpreted by the post-processing software algorithms. This signature provides definitive identification of each cartridge used in the system. The cartridge and adapter are disposable and provide on-board storage of reagents and sample overflow.

The reader is specifically designed, using an internal cartridge adapter and acceptor design track, to accommodate multiple unique cartridge configurations and form factors. This allows cartridges designed with different physical parameters to be used with the system and hence be inserted and processed. The reader, in addition to illuminating the cartridge and taking digital images may also incorporate analog and digital inputs and outputs for plug-ins, such as environmental and physiologic sensors (e.g. thermometers, gas detectors, EKG data, GPS modules, RFID readers).

The system software performs several distinct functions. These functions include the following: 1) controlling the illumination and detection algorithms; 2) creating a customizable user interface; 3) and providing pattern recognition and color mapping for conversion of optical images into quantitative graphical and numerical data. The software may be composed in C++, however, the principles behind the algorithms are programming language agnostic. The initial routine for the software is to take a single image of the cartridge when prompted through the user interface. A pre-defined region of this image is dedicated to the code or signature label that identifies the cartridge type. This is done using spectral analysis of discrete sections of the code region that in turn provides a sequence of pixel intensity values. This portion of the code sequence is compared to a database of codes to determine the remaining processing parameters and test criteria for the cartridge. In particular, this code identifies the active test and control regions of the cartridge, which defines illumination settings, defines time resolved analysis procedures, and stores lot and expiration data.

The software is also capable of being "trained" via a calibration routine in which known positives and negatives are run and a processing and calibrating algorithm is created to differentiate and quantify the degree to which a sample is positive or negative. This system is capable of, with one image, identifying the cartridge type, automatically retrieving the appropriate database of analysis parameters, and reading the test and control regions of the cartridge.

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An optical reading system comprising:
an optical reading apparatus having a test cartridge receptor to receive a test cartridge having a test strip inserted therein, the test cartridge configured to house multiple types of test strips;
wherein the optical reading apparatus includes imaging optics to produce an image of the test strip;
wherein the optical reading apparatus includes a memory device that includes instructions to select an image processing technique from a plurality of image processing techniques based on data related to the test strip;
wherein the memory device includes instructions to determine an optical test criterion based upon the selected image processing technique; and
wherein the memory device includes instructions to compare the image with the optical test criterion; and
a location detection module, wherein the location detection module is a global positioning system (GPS) receiver.

2. The optical reading system of claim 1, wherein the test strip is selected from a group consisting of lateral flow immunoassays, dry chemistry strips, chemical dipsticks, chemical rapid tests, biological rapid tests, DNA biochips, and protein biochips.

3. The optical reading system of claim 1, wherein the optical test criterion comprises a shape.

4. The optical reading system of claim 1, further comprising a display to display the image, wherein the image shows a first region of the test strip and a second region of the test strip, the first region comprising a control region and the second region comprising a sample testing region.

5. The optical reading system of claim 1, further comprising a multipurpose portable computational circuitry, the optical reader separable from the multipurpose portable computational circuitry, the multipurpose portable computational circuitry including a display device.

6. An optical reading system comprising:
an optical reading apparatus having a test cartridge receptor configured to receive a first type of test cartridge having a first test strip inserted therein and configured to receive a second type of test cartridge having a second test strip inserted therein;
wherein the optical reading apparatus includes imaging optics to produce a first image of the first test strip and a second image of the second test strip;
instructions to select a first image processing technique from a plurality of image processing techniques based on data related to the first strip and to select a second image processing technique from the plurality of image processing techniques based on data related to the second strip;
instructions to determine a first optical test criterion based upon the first image processing technique and a second optical test criterion based on the second image processing technique;
instructions to compare the first optical test image with the first optical test criterion and to compare the second optical test image with the second optical test criterion, and
a location detection module, wherein the location detection module is a global positioning system (GPS) receiver.

7. The optical reading system of claim 6, wherein the optical reading apparatus is separable from a computer device having a display portion and wherein at least one of the first image and the second image is displayed at the display portion when the optical reading apparatus is coupled to the computer device.

8. The optical reading system of claim 6, wherein the first type of test cartridge has a first width and a first depth and the second type of test cartridge has a second width and a second depth and wherein the test cartridge receptor has a single opening to receive each of the first type of test cartridge and the second type of test cartridge without use of a separate adapter.

9. The optical reading system of claim 6, wherein the test cartridge receptor includes an internal track guide for positioned insertion of test cartridges having a plurality of widths and depths.

10. The optical reading system of claim 6, wherein the optical reading apparatus includes cartridge detection and identification logic to detect receipt of a test cartridge and to determine a type of a test cartridge received into the test cartridge receptor.

11. The optical reading system of claim 6, wherein the test cartridge receptor has a side insertion track for receiving test cartridges.

12. The optical reading system of claim 6, wherein the location detection module provides location data that is communicated to a computer device when the computer device is coupled to the optical reader.

13. The optical reading system of claim 6, further comprising an environmental sensor to detect environmental conditions.

14. The optical reading system of claim 13, wherein the environmental conditions includes humidity and temperature data, airborne contaminants, and toxins.

15. An optical reading system comprising:
an optical reading apparatus having a test cartridge receptor configured to receive a first type of test cartridge having a first test strip inserted therein and configured to receive a second type of test cartridge having a second test strip inserted therein;
wherein the optical reading apparatus includes imaging optics to produce a first image of the first test strip and a second image of the second test strip;
instructions to select a first image processing technique from a plurality of image processing techniques based on data related to the first strip and to select a second image processing technique from the plurality of image processing techniques based on data related to the second strip;
instructions to determine a first optical test criterion based upon the first image processing technique and a second optical test criterion based on the second image processing technique;
instructions to compare the first optical test image with the first optical test criterion and to compare the second optical test image with the second optical test criterion, and
an environmental sensor to detect environmental conditions, wherein the environmental conditions includes humidity and temperature data, airborne contaminants, and toxins.

* * * * *